United States Patent [19]
Hill

[11] Patent Number: 5,902,547
[45] Date of Patent: May 11, 1999

[54] METHOD FOR DISINFECTING A TAGGING GUN NEEDLE

[75] Inventor: Bryan D. Hill, 5502 Gate Post Ct., Greensboro, N.C. 27455

[73] Assignee: Bryan D. Hill, Greensboro, N.C.

[21] Appl. No.: 08/627,427

[22] Filed: Apr. 4, 1996

[51] Int. Cl.$^6$ .................................. A61L 2/18; B08B 3/08
[52] U.S. Cl. .......................... 422/28; 422/294; 227/67; 604/199; 134/170
[58] Field of Search ............................ 422/28, 294, 300, 422/301; 604/199, 323, 403, 192; 227/67, 156; 173/65, 73; 134/170, 22.1, 22.11

[56] References Cited

U.S. PATENT DOCUMENTS

| | | | |
|---|---|---|---|
| 2,888,924 | 6/1959 | Dunmire | 604/199 X |
| 3,354,881 | 11/1967 | Bloch | 604/199 X |
| 4,362,241 | 12/1982 | Williams | 422/300 X |
| 4,666,436 | 5/1987 | McDonald et al. | |
| 4,767,412 | 8/1988 | Hymanson | 604/192 |
| 5,427,234 | 6/1995 | Upchurch | 604/199 X |
| 5,447,684 | 9/1995 | Williams | 422/292 X |
| 5,472,130 | 12/1995 | Beringhause et al. | 227/67 |

OTHER PUBLICATIONS

McCulloch, Ernest C. Disinfection and Sterilization, 2nd ed., p. 93, 1945.
Block, Seymour S. Disinfection, Sterilization, and Preservation, 4th ed., p. 67, 1991.

Primary Examiner—E. Leigh Mckane
Attorney, Agent, or Firm—Rhodes Coats & Bennett, L.L.P.

[57] ABSTRACT

A method for disinfecting a needle of a tagging gun is disclosed. The device used in the method includes a container having sides, a bottom and an open end opposite the bottom. A user breakable capsule is located inside the container with a liquid disinfectant inside the capsule. A needle penetratable seal seals the open end of the container until such time as the device is needed. When the capsule is broken, the disinfectant is released into the container and the tagging gun needle is pushed through the seal into contact with the disinfectant. In the preferred embodiment, a finger guard is attached adjacent to the open end of the container for helping to prevent the user from contacting the point of the needle.

1 Claim, 1 Drawing Sheet

METHOD FOR DISINFECTING A TAGGING GUN NEEDLE

BACKGROUND OF THE INVENTION (1) Field of the Invention

The present invention relates generally to a device for disinfecting needles and, more particularly, to a device for disinfecting tagging gun needles.

(2) Description of the Prior Art

Tagging guns are used for inserting attaching members, usually formed of flexible plastic, into articles. Tagging guns comprise hollow needles which are injected into the article and usually through a tag or other object designed to be secured to that article by the attachment member. Tagging guns include a plunger which reciprocates through the needle to insert the head of the flexible plastic member through the article to a position on the far side of the article. Examples of such tagging guns are shown in U.S. Pat. No. 3,103,666, issued to Bone and U.S. Pat. No. 5,472,130 issued to Beringhause et al, the entire disclosures of which are hereby incorporated by reference.

However, due to the nature of a tagging gun being hand-held and having a sharp point, it is not unusual for an operator to occasionally prick her finger or some other part of her body and draw blood. This is made more serious by the fact that more than one operator may use the same gun at different shifts and that infectious diseases including tuberculosis and HIV have become the #3 killer in the United States following heart disease and cancer.

One solution to this problem is to clean the tagging gun needle before use. This has generally been done in a separate cleaning station and requires the operator to remove the needle from the gun. One example of such a cleaning station is shown in U.S. patent application Ser. No. 29/025,785, now U.S. Pat. No. Des. 373,198, issued Aug. 27, 1996. Removing the needle from the gun itself is a potentially dangerous event and cleaning the needle along does not clean the plunger located in the needle for pushing the plastic member through the article.

While it is conceivable that the tagging gun and needle could be cleaned by immersing the needle portion of the gun in an open container of a disinfectant or that a disinfectant could be physically sprayed on the end of the gun from an aerosol can of disinfectant, disinfectants, particularly of the type necessary to effectively kill the more virulent strains of bacteria and viruses, are in themselves toxic. Such materials can cause burning of the skin or eyes or other injuries, and leaving an open container or pan of disinfectant or spraying the disinfectant in the air could, in itself, result in serious injury.

Single or multiple use medicament applicators have been known for a number of years. One such example is known by the trademark STING KILL® (medicinal preparation for external use for relief of stings and bites of poisonous insects and effects of irritating plants) and was developed by Medical Supply Company of Rockford, Ill. in the mid-60's. This device was a self-contained disposable swab-type medication applicator. One such example of such a swab applicator is shown in U.S. Pat. No. 3,958,571. Other types of such applicators have used either a removable protective cap or an encapsulated medicament within the applicator.

Finally, vials containing one or more dosages of a medicament, such as a vaccine, in which a syringe may be pushed directly through the top of the container without removing the top of the container have been utilized for a number of years. However, such devices have not been used to disinfect needles of tagging guns and, in addition, provide no means of preventing the user from pricking her finger with the needle while using the medicament vial.

Thus, there remains a need for a new and improved tagging gun needle disinfectant device which permits the safe and effective disinfectant in cleaning of a tagging gun needle while, at the same time, provides means for preventing the operator from pricking her finger with an unclean needle.

SUMMARY OF THE INVENTION

The present invention is directed to a device for disinfecting a needle of a tagging gun or the like. The device includes a container having sides, a bottom and an open end opposite the bottom. A user breakable capsule is located inside the container with a liquid a disinfectant inside the capsule. A needle penetratable seal seals the open end of the container until such time as the device is needed.

In operation, the capsule is broken to release the disinfectant and the tagging gun needle is pushed through the seal into contact with the disinfectant.

In the preferred embodiment, a finger guard is attached adjacent to the open end of the container for helping to prevent the user from contacting the point of the needle.

Accordingly, one aspect of the present invention is to provide a device for disinfecting a needle. The device includes: (a) a container having sides, a bottom and an open end opposite the bottom; (b) a disinfectant located inside the container; and (c) a needle penetratable seal sealing the open end of the container, whereby the needle may be pushed through the seal into contact with the disinfectant.

Another aspect of the present invention is to provide a device for disinfecting a needle. The device including: (a) a container having sides, a bottom and an open end opposite the bottom; (b) a user breakable capsule located inside the container; (c) a disinfectant inside the capsule; and (d) a needle penetratable seal sealing the open end of the container, whereby the capsule may be broken to release the disinfectant and the needle may be pushed through the seal into contact with the disinfectant.

Still another aspect of the present invention is to provide a device for disinfecting a needle. The device includes: (a) a container having sides, a bottom and an open end opposite the bottom; (b) a user breakable capsule located inside the container; (c) a disinfectant inside the capsule; (d) a needle penetratable seal sealing the open end of the container, whereby the capsule may be broken to release the disinfectant and the needle may be pushed through the seal into contact with the disinfectant; and (e) a finger guard attached adjacent to the open end of the container for preventing the user from contacting the point of the needle.

These and other aspects of the present invention will become apparent to those skilled in the art after a reading of the following description of the preferred embodiment when considered with the drawings.

DESCRIPTION OF THE PREFERRED EMBODIMENTS

Figure 1:
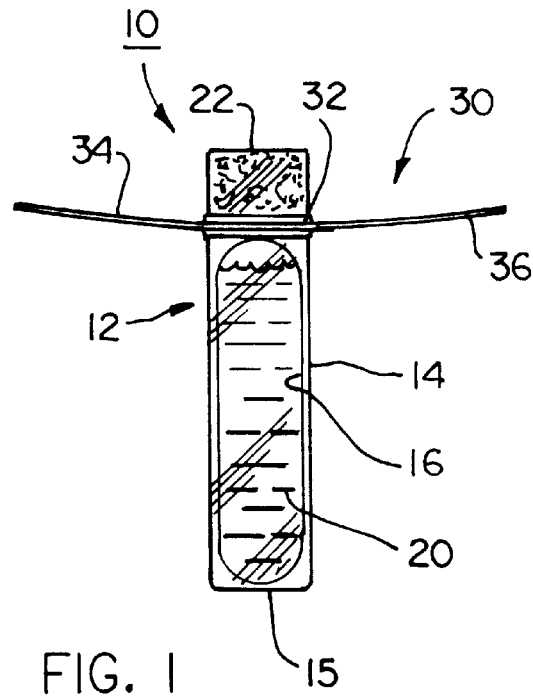
FIG. 1 is side view of a tagging gun disinfectant device constructed according to the present invention.

In the following description, like reference characters designate like or corresponding parts throughout the several views. Also in the following description, it is to be understood that such terms as "forward", "rearward", "left", "right", "upwardly", "downwardly", and the like are words of convenience and are not to be construed as limiting terms.

Referring now to the drawings in general and FIG. 1 in particular, it will be understood that the illustrations are for the purpose of describing a preferred embodiment of the invention and are not intended to limit the invention thereto. As best seen in FIG. 1, a tagging gun needle disinfectant device, generally designated 10, is shown constructed according to the present invention. The tagging gun needle disinfectant device 10 includes two major sub-assemblies: a vial 12 containing a medicament and a finger guard 30 for helping to prevent the user from pricking her finger.

Vial 12 includes a compressible plastic container 14 having an open end, generally cylindrical side walls, and an enclosed bottom 15. In the preferred embodiment, a crushable glass capsule 16 within container 14 includes at least one dosage of disinfectant 20. The end of the container opposite the bottom 15 includes a swab 22 which, in the preferred embodiment, is a liquid-absorbing fabric which is penetrable by the tagging gun needle. In an alternative embodiment, swab 22 is formed of a penetrable elastomeric material, such as rubber. In still another embodiment of the present invention, swab 22 is a cap of thin metal foil.

In the preferred embodiment, disinfectant 20 is an EPA approved disinfectant such as EPA Restriction No. 1043-36 (EPA EST.8668-IL-1). This material is generally known as an aqueous phenolic germicidal and includes #2 phenylphenol; o-benzyl-p-chlorophenol; and isopropanol. In an additional alternative embodiment of the present invention, a cleanser or lubricant is added to the disinfectant solution to aid in the maintenance of the tagging gun.

In the preferred embodiment, the present invention also includes a finger guard 30. Finger guard 30 is attached to the vial 12 by attachment ring 32. Guard 30 may be removable to allow for multiple uses or may remain attached for a single use.

Figure 2:
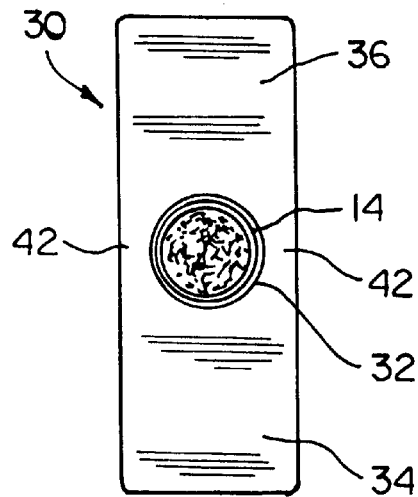
FIG. 2 is a top view of the disinfectant device shown in FIG. 1.

As best seen in FIG. 2, there is shown in top view of the disinfectant device shown in FIG. 1. Finger guard 30 is a single element forming an upper shield 34 and a lower shield 36. In addition, borders 42 may extend between the upper and lower shields to increase the area of protection of the finger guard 30.

While the preferred embodiment is generally rectangular, other geometric shapes such as ovals, squares, or circles, could be arrived at for a particular situation requiring special protection. Also, in the preferred embodiment, finger guard 30 is formed of a flexible plastic sheet, but other materials, including paper, could be utilized to protect the fingers of the user.

Figure 3:
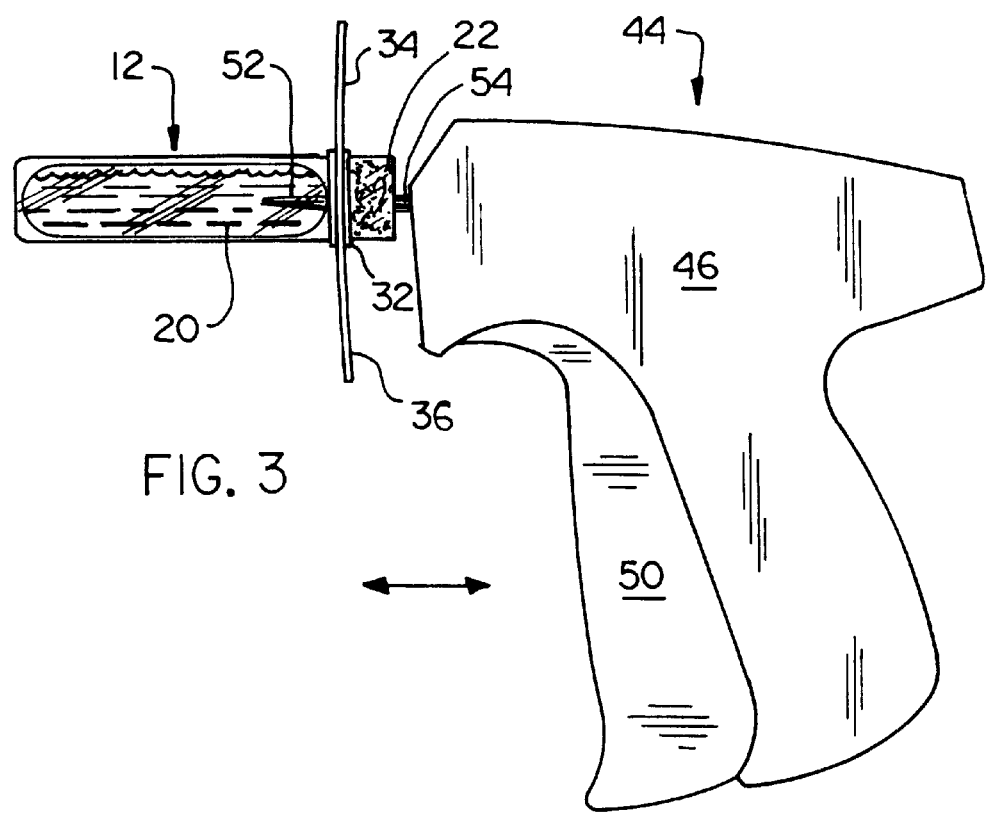
FIG. 3 is a side view of the disinfectant device used to clean a tagging gun.

Turning now to FIG. 3, there is shown a side view of the tagging gun needle disinfectant device of the present invention being used to clean a tagging gun. In operation, the operator removes the vial 12 from a sealed package (not shown) and crushes the enclosed capsule 16 between her fingers to release the disinfectant 20 into the container 14. A conventional tagging gun, generally designated 44, including a body 46, a trigger 50, a needle 52 and a plunger 54 is then picked up and needle 52 is inserted through swab 22 into disinfectant 20. The operator then pulls the trigger 50 several times which causes plunger 54 to reciprocate inside needle 52, thereby cleaning both the needle 52 and the plunger 54 at the same time. Vial 12 is then removed and disposed of properly. During the time in which the vial 12 is inserted or removed from the needle, upper and lower shields 34,36 help to prevent the operator from accidentally pricking her fingers.

Certain modifications and improvements will occur to those skilled in the art upon a reading of the foregoing description. By way of example, while the device is designed to be utilized by hand, the process could be automated or the device could be held in a fixture. It should be understood that all such modifications and improvements have been deleted herein for the sake of conciseness and readability but are properly within the scope of the following claims.

I claim:

1. A method for disinfecting a tagging gun needle and plunger, the tagging gun including a body, a trigger, a needle and a plunger, said method comprising the steps of:

(a) providing a tagging gun including a body with a trigqer, and a needle and a plunger to be disinfected;

(b) providing a compressible plastic container having sides, a bottom and an open end opposite said bottom; a user breakable capsule located inside said container; disinfectant inside said capsule; and a needle penetratable seal sealing said open end of said container;

(c) breaking said capsule to release said disinfectant into said container; and (d) pushing the needle and plunger through said seal into contact with said disinfectant in said container while the body and trigger remain outside said container; and (e) pulling said trigger to reciprocate said plunger inside said needle, thereby disinfecting both the needle and the plunger.

* * * * *

UNITED STATES PATENT AND TRADEMARK OFFICE
CERTIFICATE OF CORRECTION

PATENT NO. : 5,902,547
DATED : May 11, 1999
INVENTOR(S) : Bryan D. Hill

It is certified that error appears in the above—identified patent and that said Letters Patent is hereby corrected as shown below:

In Claim 1 (a), line 2, "trigqer" should be "trigger".

Signed and Sealed this

Twelfth Day of October, 1999

Attest:

Q. TODD DICKINSON

Attesting Officer

Acting Commissioner of Patents and Trademarks